United States Patent
Boon et al.

(10) Patent No.: US 9,125,528 B2
(45) Date of Patent: *Sep. 8, 2015

(54) MAKE-UP REMOVAL WIPE

(71) Applicant: Kimberly-Clark Worldwide, Inc., Neenah, WI (US)

(72) Inventors: Jason Robert Boon, Appleton, WI (US); Frederick Juan Williams, Jr., Cumming, GA (US); Walter George Bauer, Neenah, WI (US); Kevin Christopher Possell, Middleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/541,984

(22) Filed: Nov. 14, 2014

(65) Prior Publication Data

US 2015/0089761 A1  Apr. 2, 2015

Related U.S. Application Data

(63) Continuation of application No. 13/742,333, filed on Jan. 15, 2013, now Pat. No. 8,914,936.

(60) Provisional application No. 61/596,511, filed on Feb. 8, 2012.

(51) Int. Cl.
| | |
|---|---|
| *A45D 40/00* | (2006.01) |
| *A47K 7/02* | (2006.01) |
| *A47L 13/16* | (2006.01) |
| *D04H 1/00* | (2006.01) |

(52) U.S. Cl.
CPC . *A47K 7/02* (2013.01); *A45D 40/00* (2013.01); *D04H 1/00* (2013.01); *A45D 2200/1063* (2013.01); *A47L 13/16* (2013.01)

(58) Field of Classification Search
CPC ....... A45D 33/34; A45D 40/26; A45D 40/28; A45D 44/00; A45D 2200/1009; A45D 2200/1018; A45D 2200/1054; A45D 2200/1063; A47L 13/10; A47L 13/16; A47K 7/00; A47K 7/02; A47K 7/03
USPC ................ 15/208, 209.1, 210.1, 223, 229.14, 15/244.1, 244.4; 132/320; D4/137; D28/4, D28/7, 8, 9, 63; D32/35, 40

See application file for complete search history.

(56) References Cited

U.S. PATENT DOCUMENTS

| | | | | |
|---|---|---|---|---|
| 2,528,812 | A | * | 11/1950 | Berman ...................... 15/229.14 |
| 2,841,811 | A | * | 7/1958 | Carroll ......................... 15/244.1 |

(Continued)

FOREIGN PATENT DOCUMENTS

| | | | |
|---|---|---|---|
| JP | 2002-315707 | * | 10/2002 |
| JP | 2006-68469 | * | 3/2006 |

*Primary Examiner* — Mark Spisich
(74) *Attorney, Agent, or Firm* — Kimberly-Clark Worldwid, Inc.

(57) ABSTRACT

To better facilitate the application and removal of make-up on the skin, including on the face, and especially around the eyes, the present invention provides a wiping product having two or more lobes which substantially conform to both the user's finger and the area around the user's eyes. The wiping product is not secured to the user's finger or worn like a glove, but rather is simply supported by one or more fingers in use. In this manner, the wiping product is both simple to use and provides excellent application and removal of make-up in often hard to reach areas, such as the recesses of the eyes.

13 Claims, 7 Drawing Sheets

(56) References Cited

U.S. PATENT DOCUMENTS

| | | | |
|---|---|---|---|
| 3,122,768 A | * | 3/1964 | Beumkes .................... 15/244.1 |
| 3,204,277 A | * | 9/1965 | Visman et al. ............... 15/244.1 |
| D271,817 S | * | 12/1983 | Collin ........................... D32/40 |
| 2005/0050667 A1 | * | 3/2005 | Higgins et al. ............... 15/244.4 |
| 2005/0257805 A1 | * | 11/2005 | Williams ...................... 132/320 |

* cited by examiner

MAKE-UP REMOVAL WIPE

RELATED APPLICATIONS

The present application is a continuation application and claims priority to U.S. patent application Ser. No. 13/742,333, filed on Jan. 15, 2013, now U.S. Pat. No. 8,914,936, which claims priority to U.S. Provisional Application No. 61/596,511, filed Feb. 8, 2012, the contents of which are hereby incorporated by reference in a manner consistent with the present application.

BACKGROUND

Typically the application and removal of eye make-up and other cosmetics is performed with cotton pads, cotton balls, or non-woven wipes so as to apply or remove the composition by lightly rubbing the skin. These products are often square or round in shape and poorly adapted to removing or applying make-up around the eyes. Moreover, when a user wishes to remove make-up from her eyelashes using a cotton or non-woven pad impregnated with a make-up remover composition, a large proportion of the composition remains in the pad without contributing to removal of the make-up. Also, any make-up that is partially dissolved by the remover composition becomes trapped in the fibers, fouling the pad, shortening its life and making removal less effective.

These applicators are not particularly ergonomic for the removal of make-up, as the applicator is unable to adapt to the contours of the user's face, which has both concave and convex surfaces, and cannot access smaller dimensions. For instance, the application may need to be accomplished in a very precise manner so as to avoid bringing liquid into contact with the eyes or in some instances may need to be folded or otherwise adapted to wipe around the eyes. Wiping about the eyes is particularly challenging because of the many convex and concave surfaces created in part by the proximity of the nose, the curvature of the eyelids and the top and bottom rows of eyelashes which are neither the same length, nor similarly positioned, relative to the eye opening.

Accordingly, there is a need for a novel applicator facilitating the removal of make-up. Preferably, the applicator is specifically adapted to removal and application of make-up near the eye of the user.

SUMMARY

To better facilitate the application and removal of make-up on the skin, including on the face, and especially around the eyes, the present invention provides a wiping product having two or more lobes which substantially conform to both the user's finger and the area around the user's eyes. The wiping product is not secured to the user's finger or worn like a glove, but rather is simply supported by one or more fingers in use. In this manner, the wiping product is both simple to use and provides excellent application and removal of make-up in often hard to reach areas, such as the recesses of the eyes.

Accordingly, in one embodiment the present invention provides a wiping product comprising a rectangular central portion and a pair of opposed lobes continuous therewith, each lobe having a curvilinear peripheral edge.

In other embodiments the present invention provides a wiping product comprising a rectangular central portion and two pairs of opposed lobes continuous therewith, each lobe having a base that defines one side of the rectangular central portion and a bell-shaped peripheral edge that terminates in a tip distal from the base, the tip of the first pair of opposed lobes being defined by the arc of a first circle having a radius R1 and the tip of the second pair of opposed lobes being defined by the arc of a second circle having a radius R2.

In another embodiment the present invention provides a wiping product comprising a rectangular central portion and two pairs of opposed lobes continuous therewith, each lobe having a base that defines one side of the rectangular central portion and a substantially semi-circular peripheral edge, the peripheral edge defined by the arc of a circle having a radius R1.

In yet another embodiment the present invention provides a symmetrical wiping product comprising a liquid permeable nonwoven substrate, the substrate having a rectangular central portion and a curvilinear peripheral edge, the curvilinear peripheral edge defining four lobes extending from the central portion, each lobe having a convex and concave portion, the concave portion being defined by a first circle C1 having a first radius R1, the convex portion being defined by a second circle C2 having a second radius R2.

In still other embodiments the present invention provides a stack of wiping products comprising a first and a second wiping product, the wiping products each having a pair of opposed lobes bisected by a longitudinal axis, the first wiping product being stacked on top of and offset from the second wiping product such that the longitudinal axis of the first wiping product is orientated from about 5 to about 30 degrees relative to the longitudinal axis of the second wiping product.

DETAILED DESCRIPTION

The present invention provides a wiping product having multiple lobes, such as two, four or six lobes. Compared to prior art wipes, the wipe of the present invention provides the user with more useable surface area for wiping and multiple wiping surfaces. The wipe, and particularly the curvilinear shape of the wipe's peripheral edge, also permits the user to intuitively determine which portion of the wipe is best suited for wiping and to use the wipe without modifying or altering its shape. Further, because each lobe is discrete, the user may use individual lobes for different purposes. For example, a user may apply makeup with one lobe and remove makeup with another.

While the shape of the wipe makes it particularly well suited for the application and removal of makeup around the eyes, this is but one preferred use of the wipe. The wipe may be used in various applications. For example, the wipe may be used to clean or treat parts of the body such as the eyes, the ears, the nose, and the like. The wipe also may be used to apply a medicine, lotion, ointment, cleaning agent, or the like to any part of the body, or any other object. It should be appreciated however, that the aforementioned options for the use of the wipe is not intended as a limitation.

In one preferred embodiment the wiping product comprises four lobes, more preferably a pair of opposed lobes extending from a rectangular central portion. The lobes have curvilinear peripheral edges that terminate in a rounded tip that is distal from the central portion. The rounded tip is generally formed by the arc of a circle having a radius from about 5 to about 20 mm, and more preferably from about 10 to about 15 mm. The shape of the lobe, and particularly the rounded tip, allow the wipe to conform to the curvatures of a user's face and especially the eyes in use.

The components of the wipe may be made of various suitable materials. Particularly well suited materials include non-woven webs formed from synthetic and/or natural fibers. Preferably the non-woven webs are permeable to both air and liquids. However, in certain embodiments the wipe may comprise a laminate of a non-woven web and a liquid impermeable substrate.

In addition to forming the wipe from different materials, individual materials may be imparted with patterns or textures to facilitate the removal or application of make-up. For example, when used to remove make-up the wipe may include a texturized surface adapted to scrub or brush the skin of the user.

In certain embodiments the wiping product comprises a spunbond web, a coform web, a tissue web, a meltblown web, a bonded carded web, and laminates thereof. A nonwoven material can be made from various fibers, such as synthetic or natural fibers. In certain embodiments the wipes can have a dry basis weight of from about 50 to about 250 grams per square meter (gsm), more preferably from about 75 to about 200 gsm and still more preferably from about 100 to about 150 gsm.

In one embodiment, synthetic fibers, such as fibers made from thermoplastic polymers, can be used to construct the cover layer of the present invention. For example, suitable fibers could include melt-spun filaments, staple fibers, melt-spun multi-component filaments, and the like. These synthetic fibers or filaments used in making the nonwoven material may have any suitable morphology and may include hollow or solid, straight or crimped, single component, conjugate or biconstituent fibers or filaments, and blends or mixtures of such fibers and/or filaments, as are well known in the art.

The synthetic fibers may be formed from a variety of thermoplastic polymers where the term "thermoplastic polymer" refers to a long chain polymer that repeatedly softens when exposed to heat and substantially returns to its original state when cooled to ambient temperature. As used herein, the term "polymer" generally includes, but is not limited to, homopolymers, copolymers, such as for example, block, graft, random, and alternating copolymers, terpolymers, etc., and blends and modifications thereof.

Exemplary thermoplastics include, without limitation, poly(vinyl) chlorides, polyesters, polyamides, polyfluorocarbons, polyolefins, polyurethanes, polystyrenes, poly(vinyl) alcohols, caprolactams, and copolymers of the foregoing, and elastomeric polymers such as elastic polyolefins, copolyether esters, polyamide polyether block copolymers, ethylene vinyl acetates (EVA), block copolymers having the general formula A-B-A' or A-B like copoly(styrene/ethylene-butylene), styrene-poly(ethylene-propylene)-styrene, styrene-poly(ethylene-butylene)-styrene, (polystyrene/poly(ethylene-butylene)/polystyrene, poly(styrene/ethylene-butylene/styrene), A-B-A-B tetrablock copolymers, and the like.

Synthetic fibers added to the nonwoven web can also include staple fibers which can be added to increase the strength, bulk, softness and smoothness of the base sheet. Staple fibers can include, for instance, various polyolefin fibers, polyester fibers, nylon fibers, polyvinyl acetate fibers, cotton fibers, rayon fibers, non-woody plant fibers, and mixtures thereof.

Besides, or in addition to, synthetic fibers, pulp fibers can also be used to construct the cover layer. The pulp fibers used in forming the cover layer may be softwood fibers having an average fiber length of greater than 1 mm, and particularly from about 2 to 5 mm based on a length weighted average. Such fibers can include northern softwood kraft fibers, redwood fibers, and pine fibers. Secondary fibers obtained from recycled materials may also be used. In addition, hardwood pulp fibers, such as eucalyptus fibers, or thermomechanical pulp can also be utilized in the present invention.

In some embodiments of the present invention, the wipe may comprise a hydroentangled web. Hydroentangled webs, which are also known as spunlace webs, refer to webs that have been subjected to columnar jets of a fluid that cause the fibers in the web to entangle. For example, in one embodiment, the cover layer can comprise HYDROKNIT™ (Kimberly-Clark, Neenah, Wisc.) a nonwoven composite fabric that contains 70 percent by weight pulp fibers that are hydraulically entangled into a continuous filament material.

In one embodiment, the wipe may comprise a laminate containing two or more webs. For instance, the wipe may comprise a multilayered laminated web comprising spunbonded/meltblown/spunbonded laminate, a spunbonded/meltblown laminate, and the like. In a particular embodiment, the substrate may be formed from a laminate of a liquid impermeable material and an outer nonwoven cover material. The nonwoven cover material defines the top side of the wipe and may comprise any suitable fabric material, such as a woven fabric, a nonwoven fabric, or a knitted fabric. In this manner, the liquid impermeable material defines a back surface of the wipe and prevents compositions applied to the top surface of the wipe from migrating through the wipe to the user's fingers.

In still other embodiments the wipe may comprise two different layers, a first layer that is designed to apply or remove make-up and a second layer that is intended to facilitate handling of the wiping product.

As discussed previously, in certain embodiments one or more surfaces of the wipe may include a texturized surface. A texturized surface is particularly useful when the wipe is used to scrub or clean surfaces, such as the skin. In a particularly preferred embodiment the wipe comprises a single ply of non-woven synthetic material, the wipe having a top and a bottom surface where the top surface is texturized.

The manner in which a texturized surface is formed on a nonwoven web for use in the present invention can vary depending upon the particular application of the desired result. For example, in one embodiment the web may be embossed. In another embodiment the web may be matte finished to provide a texture.

In still other embodiments a texturized surface may be imparted by thermally point unbonding a nonwoven web to form a plurality of tufts. As used herein, a substrate that has been "thermally point unbonded" refers to a substrate that includes raised unbonded areas or lightly bonded areas that are surrounded by bonded regions. For example, bumps or tufts are the unbonded or lightly bonded areas that form raised projections off the surface of the nonwoven web to provide the necessary texture.

The material used for the point unbonding process can vary depending upon the particular application. For instance, the material can be a single layer or can include multiple layers of material. For most applications, the total basis weight of the material should be at least 1 osy, and particularly from about 3 to about 9 osy. Higher basis weights are needed in order to produce tufts with an appropriate height.

Besides point unbonding, other methods for creating texturized surfaces on base webs may be utilized. Examples of known nonwoven, texturized materials, include rush transfer materials, flocked materials, wireformed nonwovens, and the like. Moreover, through-air bonded fibers, such as through-air bonded bicomponent spunbond, or point unbonded materials, such as point unbonded spunbond fibers, can be incorporated into the base web to provide texture to the wipe.

Textured webs having projections from about 0.1 to about 25 mm, more preferably from about 0.2 to about 5 mm, such as pinform meltblown or wireform meltblown can also be utilized in a base web of the present invention. Still another example of suitable materials for a texturized base web includes textured coform materials. In general, "coform" means a process in which at least one meltblown diehead is arranged near a chute through which other materials are added to the web while it forms. Such other materials can include, for example, pulp, superabsorbent particles, or cellulose or staple fibers. Coform processes are described in U.S. Pat. No. 4,818,464. Webs produced by the coform process are generally referred to as coform materials.

In certain embodiments the wipe contains two nonwoven layers such as that described in U.S. Publication No. 2009/0151849. As such the wipe may comprise a first nonwoven layer having first and second opposing surfaces. The first nonwoven layer contains fibers formed from a polymer composition and is generally opaque in nature. A second nonwoven layer is laminated to the first surface of the first nonwoven layer. The second nonwoven layer contains a colorant that imparts a certain color to the second layer. Prior to use, the colored second layer is not generally visible when viewed from the second surface of the first layer due to the opaque nature of the first layer. However, bodily oils absorbed by the first layer during use can prevent light from adequately reflecting from the layer. Thus, at least a portion of the first layer becomes translucent or transparent so that the color of the second layer becomes visible to a user. This provides a variety of benefits, including the ability for a user to evaluate if or how much sebum was removed from the skin so that make-up can be applied with confidence.

As discussed previously, the shape of the wiping product make it particularly well suited for the application or removal of make-up, and the like, from the area around a user's eyes. In particular, the wiping products allow the user to easily access the recesses of the eye without incidental contact of the surrounding area or the eye itself. In this manner the wiping product generally has a shape that is adapted to the morphology of the user's face, such as a lobe extending from a central portion where the lobe has a curvilinear peripheral edge.

Generally the wipe comprises a central portion, which is preferably rectangular, and at least a pair of lobes continuous therewith. Each lobe preferably has a rounded convex tip and curvilinear sides, which may be either convex or concave. More preferably the wipe comprises a pair of opposed lobes and still more preferably two pairs of opposed lobes, the two pair of opposed lobes being arranged such that the wipe comprises alternating tips and valleys, which define the region where two adjacent lobes meet. In this manner the wiping product will generally have a width measured between the apex of one pair of opposing tips and a length measured between the apex of the other pair of opposing tips. In some embodiments the length and width will be equal, while in other embodiments they are different.

Figure 1:
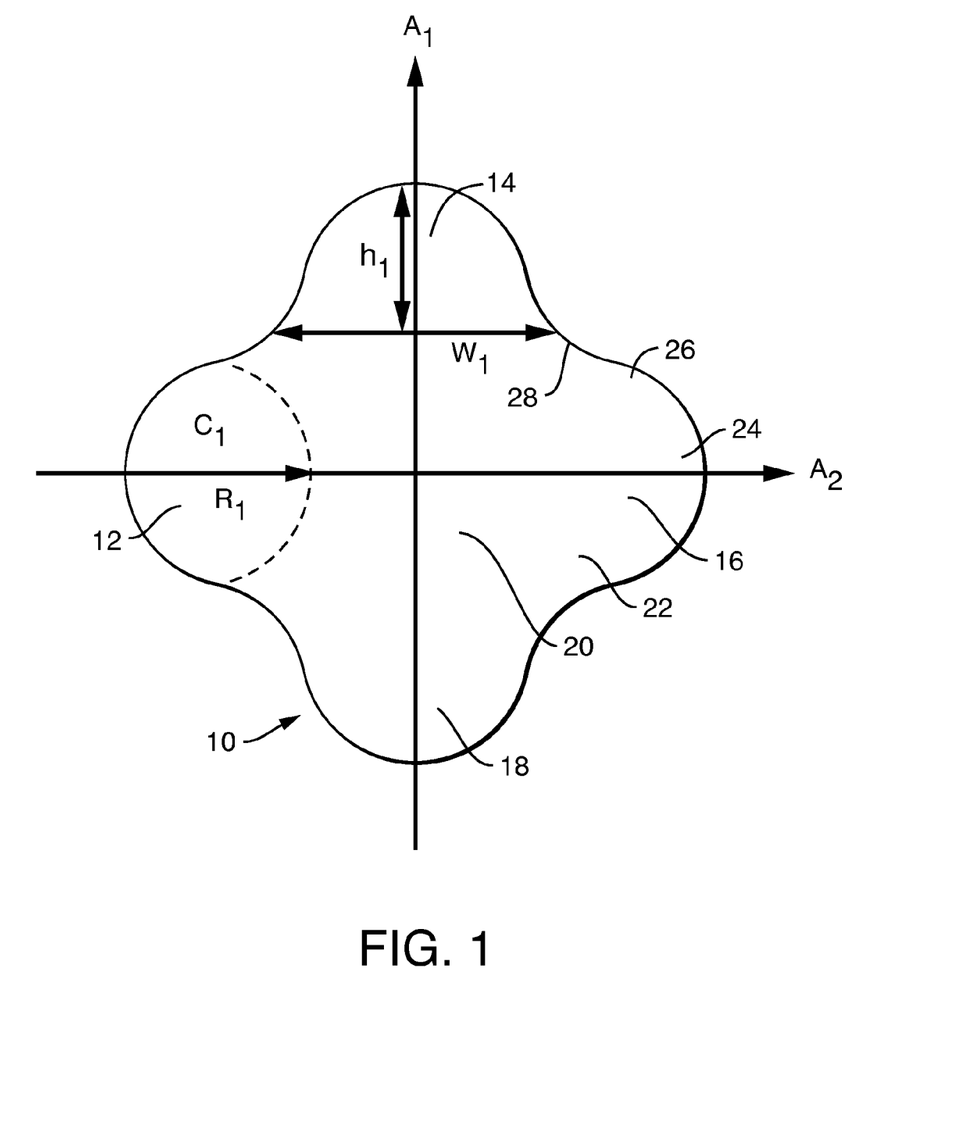
FIG. 1 is a top view illustrating one embodiment of a wiping product having four lobes.

Particularly preferred wipe shapes may be better understood with reference to the figures. For example, one embodiment of a wiping product is shown in FIG. 1, which illustrates a wiping product 10 having a central portion 20 and four lobes 12, 14, 16, 18 extending therefrom. The central portion 20 is preferably rectangular and more preferably square. The sides of the central portion, which are defined by the point at which the central portion meets the lobe, may vary from about 20 to about 50 mm and more preferably from about 30 to about 40 mm.

As further illustrated in FIG. 1, the lobes have a curvilinear peripheral edge 26 that forms a rounded tip 24. In the illustrated embodiment the peripheral edge 26 is generally bell-shaped, although in alternate embodiments it may take any number of shapes, as described below. That is, the curvilinear peripheral edge 26 has both a concave portion, which forms the tip 24, and a convex portion 28. Further, the edge of the lobe tapers inward as it extends from the base 22 to the tip 24. In certain embodiments the base 22 may have a width w1 from about 20 to about 50 mm and more preferably from about 30 to about 40 mm. Each lobe further has a height (the height of one lobe being designated as h1 in FIG. 1) defined by a line extending from the base 22 to the apex of the tip 24, bisecting the lobe into first and second portions. In certain embodiments the height may be from about 10 to about 30 mm and more preferably from about 15 to 20 mm. The heights of the lobes may be the same or may be different. For example, one lobe may have a height h1 and another may have a height h2 wherein h1 and h2 are different.

With further reference to FIG. 1, the tip 24 is defined by the arc of a circle C1 having a radius R1. In certain embodiments the radius R1 may be from about 5 to about 35 mm, more preferably from about 10 to about 30 mm and still more preferably from about 15 to about 20 mm.

While the embodiment illustrated in FIG. 1 comprises four lobes which are substantially identical in shape, the lobes may be shaped differently. For example, in certain embodiments the lobes may be shaped differently so as to provide the user with lobes of varying dimensions to aid in the application or removal of make-up. In a particularly preferred embodiment the wipe comprises two pairs of opposed lobes, the first pair of opposed lobes being substantially bell-shaped and having tips defined by the arc of a circle having a radius from about 10 to about 15 mm, and the second pair of opposed lobes also being substantially bell-shaped and having tips defined by the arc of a circle having a radius from about 15 to about 20 mm.

In still other embodiments the wipe comprises a central portion and two pairs of bell-shaped opposed lobes. The first pair of bell-shaped lobes has a base that is about 35 mm and a tip distal to the base that is defined by the arc of a circle having a radius of about 10 mm. The second pair of bell-shaped lobes also has a base that is about 35 mm, however the distal tip is defined by the arc of a circle having a radius of about 13 mm. In this manner the wipe has lobes of differing size and shape, which provide the user with a variety of wiping options when applying or removing make-up.

While the dimensions of the lobes and central area may vary, generally the total surface area of the wipe is from about 10 to about 20 cm$^2$, more preferably from about 12 to about 15 cm$^2$. Preferably the central portion comprises less than about 50 percent of the total area of the wipe, such as from about 20 to about 50 percent and more preferably from about 30 to about 40 percent. The remainder of the surface of the wipe is made up of the lobes, which preferably comprise greater than about 50 percent of the total area of the wipe, such as from about 50 to about 80 percent and more preferably from about 60 to about 70 percent. Configured in this manner, the wiping product ensures the proper size and shape for optimized wiping of hard to reach areas and further ensures that the user does not need to manipulate the wipe by folding or bending to access such areas.

Figure 2:
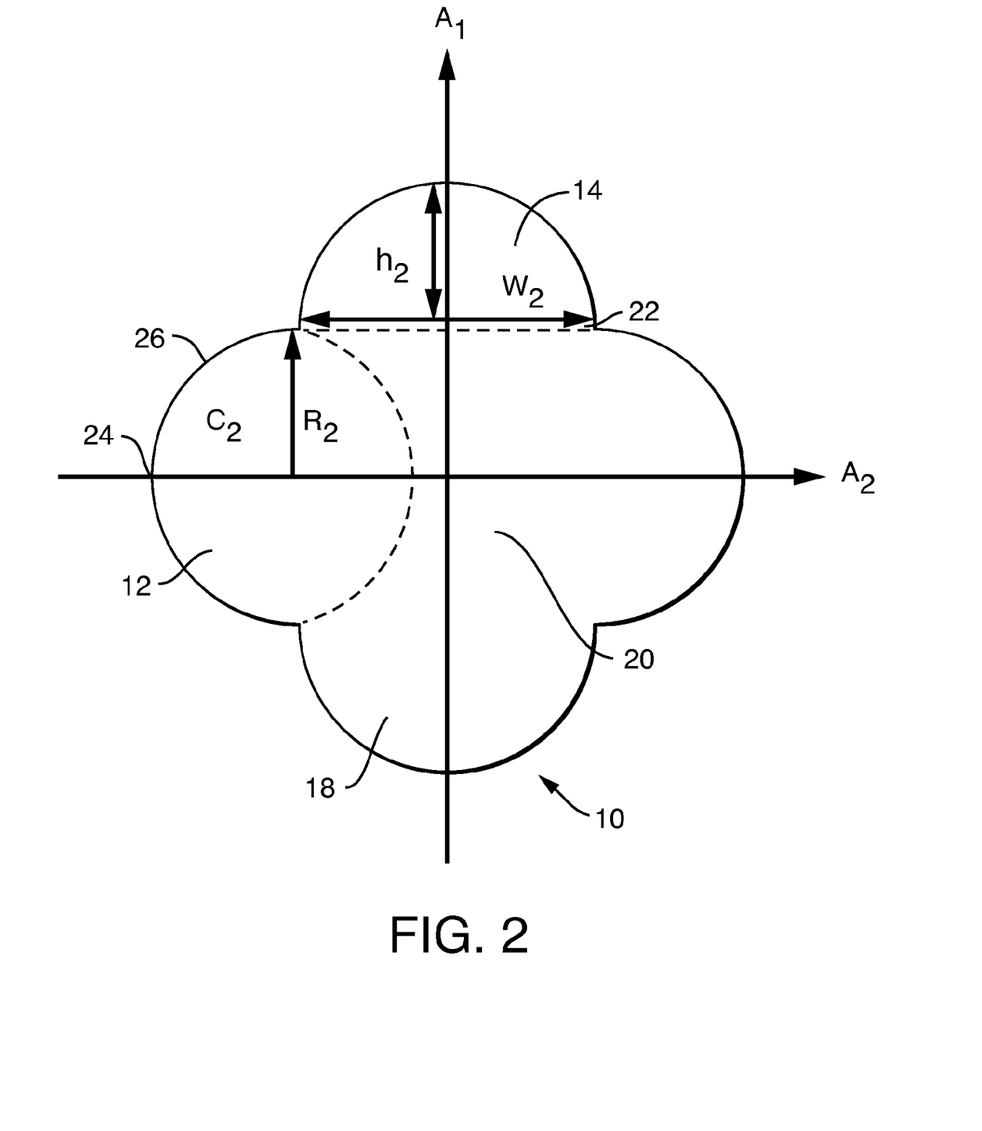
FIG. 2 is a top view illustrating an alternate embodiment of a wiping product having four lobes.

In another embodiment, illustrated in FIG. 2, the wipe comprises lobes that are semicircular in shape rather than bell-shaped. Accordingly, the wipe 10 may comprise a pair of opposed semicircular lobes 12, 14 and 16, 18 continuous with a rectangular central portion 20. Preferably the semicircular lobes have similar dimensions; however, they may be different dimensions. Regardless of the specific dimensions, each lobe has a curvilinear peripheral edge 26 defined by the arc of a circle C2 having a radius R2. In certain embodiments the radius R2 may be from about 10 to about 30 mm and more preferably from about 15 to 20 mm. Each lobe has a base 22 that defines one side of the central portion 20. The base may have a width W2 from about 20 to about 50 mm and more preferably from about 30 to about 40 mm.

Figure 3:
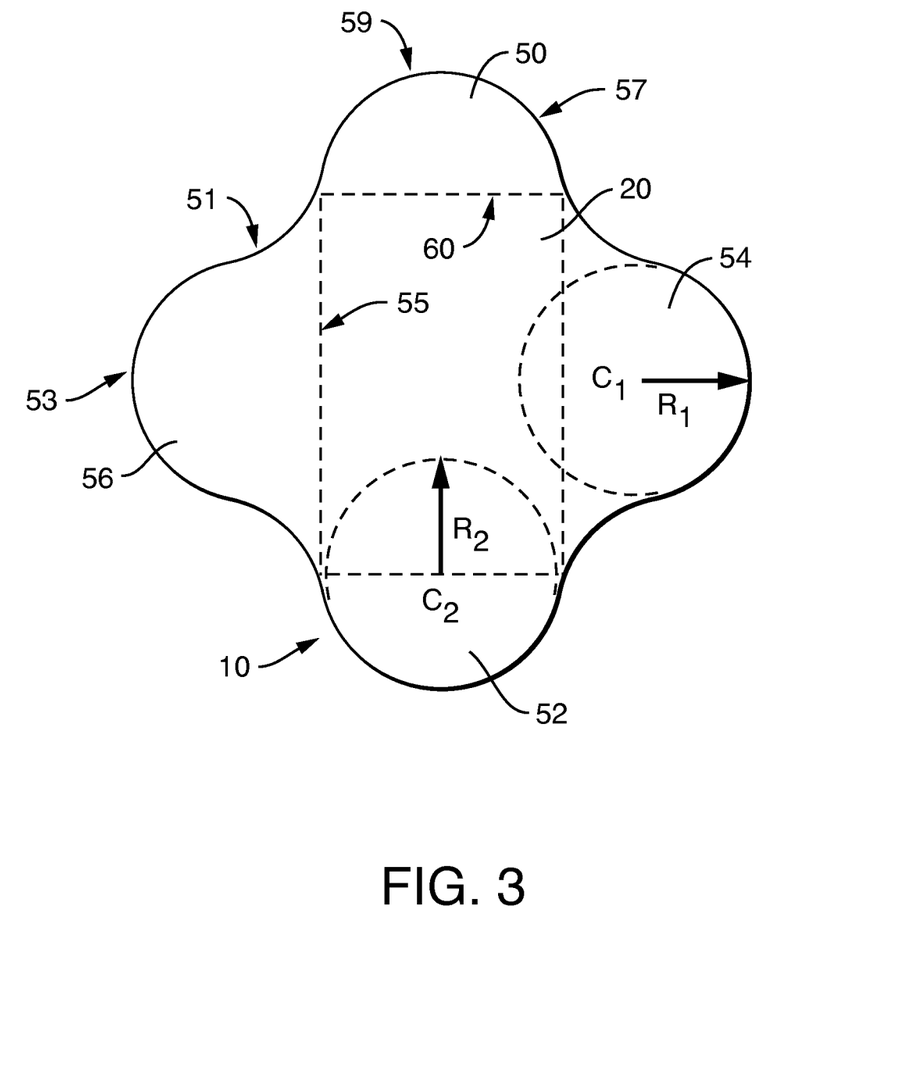
FIG. 3 is a top view illustrating another embodiment of a wiping product having two pairs of opposing lobes.

In still other embodiments, such as the embodiment illustrated in FIG. 3, the wipe 10 may comprise two pairs of opposed lobes 50, 52 and 54, 56 having both different shapes and dimensions. For example, the wipe 10 may comprise a rectangular central portion 20 and two pairs of opposing lobes 50, 52 and 54, 56 continuous therewith. The first pair of lobes 54, 56 may be substantially bell-shaped such that the peripheral curvilinear edge has a portion that is concave 53 and another portion that is convex 51. The concave portion 53 forms the tip of the lobe, which is defined by the arc of a circle C1 having a radius R1. The second pair of lobes 52, 54 are substantially semi-circular in shape with a curvilinear peripheral edge 57 that extends from the base 60 to form the arc of a circle C2 having a radius R2. The radii R1 and R2 may be the same or may be different.

Figure 4:
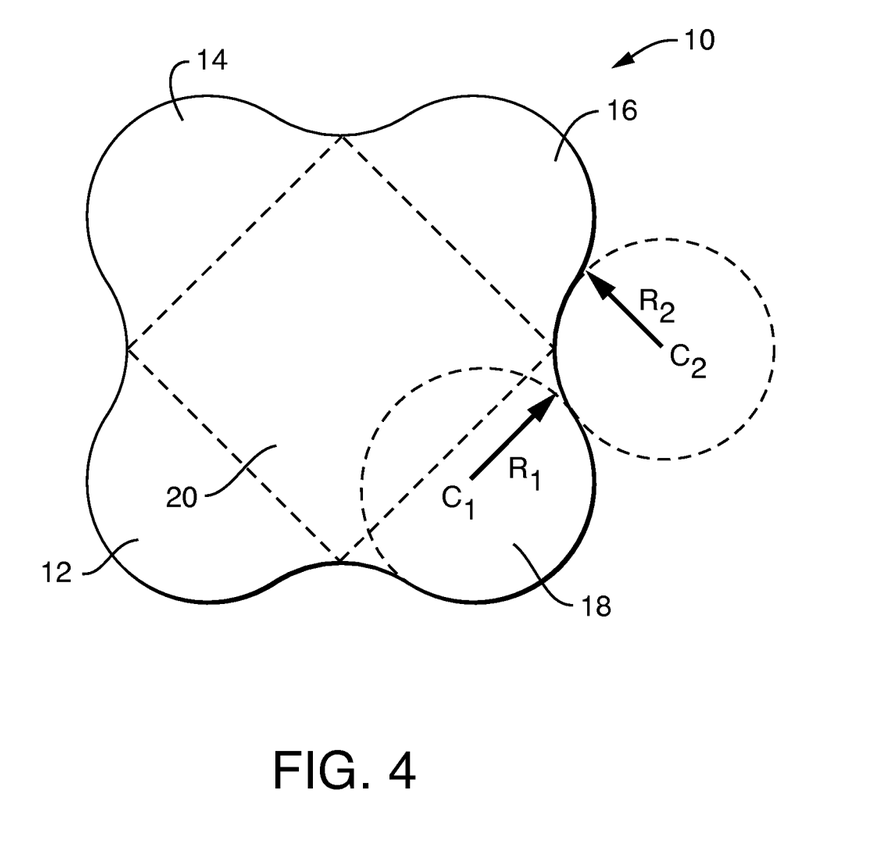
FIG. 4 is a top view illustrating still another embodiment of a wiping product having four similarly shaped lobes.

In particularly preferred embodiments, such as the embodiment illustrated in FIG. 4, the wipe 10 is symmetrical and comprises four bell shaped lobes 12, 14, 16, 18 having substantially the same size and shape. The inventors have surprising discovered that four equal bell shaped lobes extending from a rectangular central portion, where the lobes comprise from greater than about 50 percent of the surface area of the wipe, provide the optimal wiping substrate for applying or removing makeup around the eye. For example, the wipe 10 preferably comprises a rectangular central portion 20 and four bell-shaped lobes continuous therewith. That is, each lobe has a concave tip that is defined by a circle C1 having a radius R1. In this embodiment the tip of each lobe has an equal radius of curvature, that is, R1 is the same for each lobe. The tip of each lobe is separated from the next by a concave curvilinear edge, the concave portion of which is defined by a circle C2 having a radius R2. In this embodiment the concave portion of each lobe has an equal radius of curvature, that is, R2 is the same for each lobe.

In addition to varying the size and shape of the outer periphery of the wipe to alter its appearance, the wipe may be embossed or otherwise treated to create a textured surface.

Figure 5:
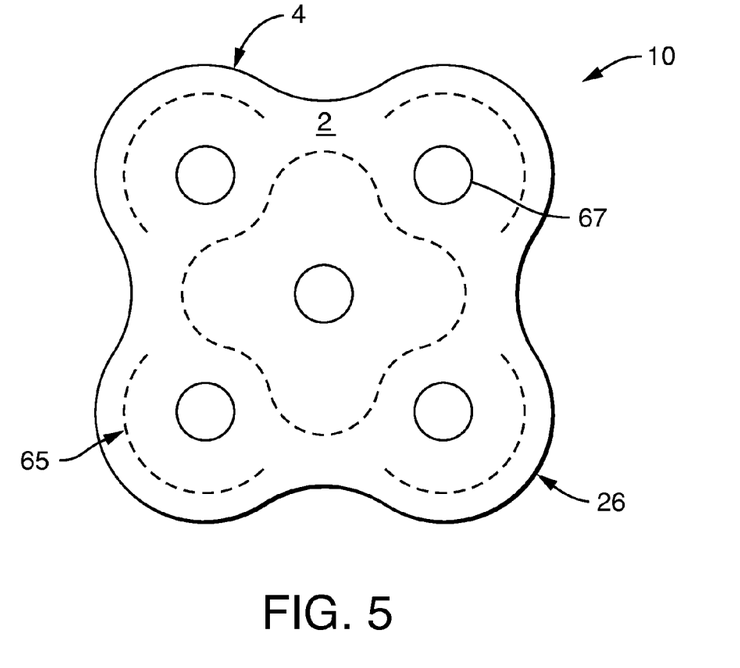
FIG. 5 is a top view illustrating one example of an embossing pattern disposed on a wiping product.
Figure 6:
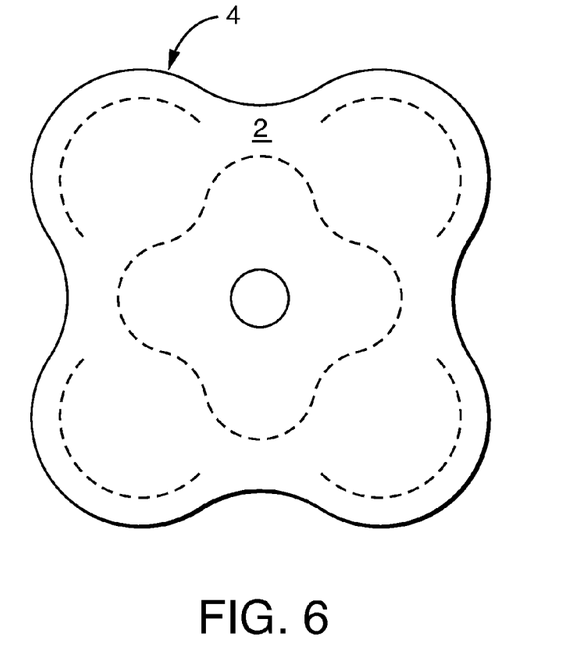
FIG. 6 is a top view illustrating another example of an embossing pattern disposed on a wiping product.
Figure 7:
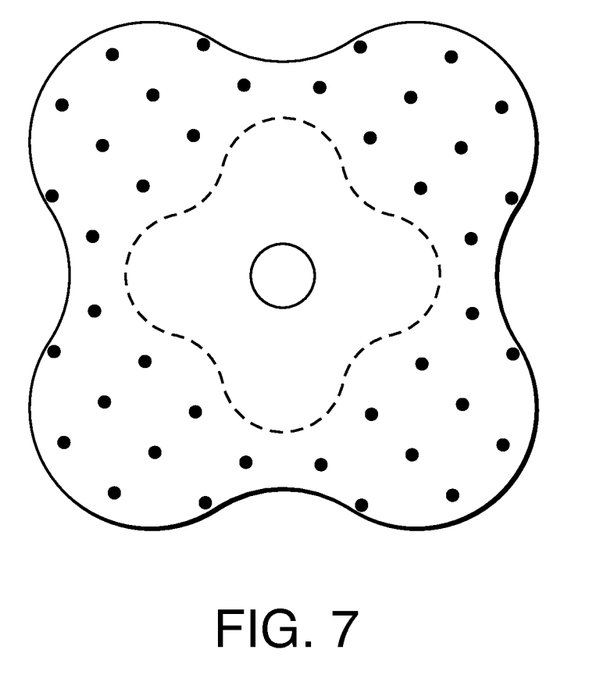
FIG. 7 is a top view illustrating still another example of an embossing pattern disposed on a wiping product.

While the textured surface may take on any particular pattern, three particularly preferred patterns are illustrated in FIGS. 5, 6 and 7. For example, as illustrated in FIG. 5, the wipe 10 may have a plurality of embossments 65, 67 disposed thereon, interior to the peripheral edge 26. The embossments may be either discontinuous embossing elements 65 or continuous embossing elements 67, or a combination thereof. In a particularly preferred embodiment, the embossments are disposed on only one surface of the wiping product. Therefore, in a preferred embodiment for a wiping product 10 having a top surface 2 and a bottom surface 4, the embossments are disposed only on the top or bottom surface.

Regardless of the specific shape of the lobes or the overall shape and appearance of the wipe, it is preferred that the wipe is bisected by at least one, and more preferably two, axis. Preferably the axis bisects the wipe, including the lobes, into symmetrical halves. For example, with reference to FIG. 1, the wipe has a longitudinal axis A1, which bisects the first and second lobes 14 and 18 into substantially equal halves, and a horizontal axis A2, which bisects the third and fourth lobes 12 and 16 into substantially equal halves. In those embodiments where the wipe comprises two pairs of opposed lobes, which are divided by a horizontal and a longitudinal axis, it is preferred that the axes are orientated about 90 degrees relative to one another.

Where a plurality of wipes of the present invention are provided to consumers as a stack of wipes, i.e., two or more wipes stacked on top of one another, the axis of adjacent wipes are preferably offset from one another. Offsetting the axis of adjacent wipes enables individual lobes to remain accessible to a user and improves dispensing.

Figure 8:
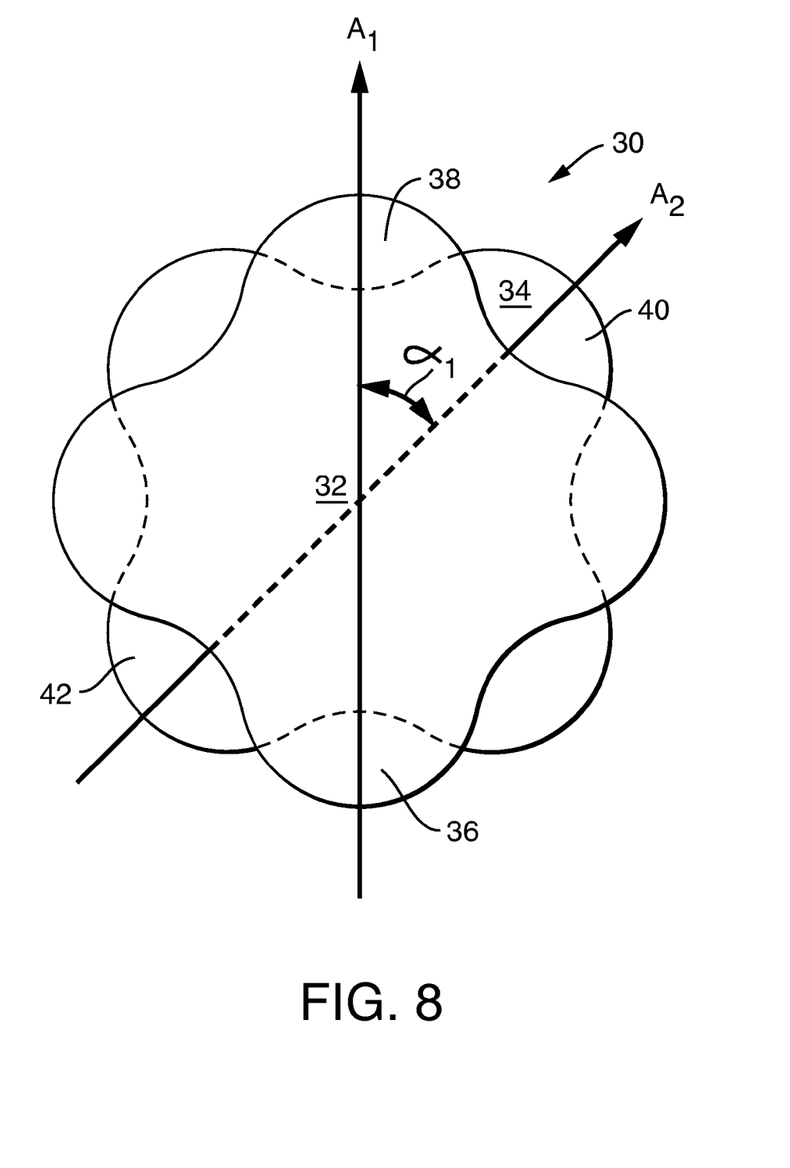
FIG. 8 is a top view illustrating two wiping products stacked on top of one another for improved dispensing.

Preferably a plurality of wipes is provided wherein each wipe has a peripheral edge defining a pair of opposed lobes bisected by a longitudinal axis, the wipes being stacked on top of one another and offset such that the longitudinal axis of adjacent wipes are orientated from about 2 to about 60 degrees, more preferably from about 5 to about 40 degrees and still more preferably from about 10 to about 30 degrees, relative to one another. For example, FIG. 8 illustrates a stack of wipes 30 comprising a first wipe 32 having a pair of opposed lobes 36, 38 bisected by a vertical axis A1, disposed on top of a second wipe 34 having a pair of opposed lobes 40, 42 bisected by a vertical axis A2. The vertical axis A2 is offset from the vertical axis A1 by an angle ($\alpha$) that is preferably from about 2 to about 60 degrees, more preferably from about 5 to about 40 degrees and still more preferably from about 10 to about 30 degrees. In this manner the lobes 40, 42 of the second wipe 34 are visible and accessible to the user even when the first wipe 32 remains on top. Arrangement of stacked wipes in this manner improves dispensing as a free edge remains visible and accessible to the user. While a wipe having multiple lobes itself provides improved dispensing over prior art circular lobes, dispensing is improved even more by offsetting stacked lobes in this manner.

While offsetting successive wipes within a stack generally provides for improved dispensing, dispensing may be optimized by selecting an offset angle that minimizes sagging of the offset lobes. Because the lobes of adjacent wipes are at least partially unsupported when wipes are offset from one another, too great of an offset angle ($\alpha$) may actually lead to poorer dispensing. Thus, in a preferred embodiment the offset angle ($\alpha$) is from about 3 to about 30 degrees and more preferably from about 5 to about 20 degrees, so as to adequately support the lobes of adjacent wipes in a stack and provide superior dispensing.

The stack of wipes can include any suitable number of individual wipes depending upon the desired packaging and end use. For example, the stack can be configured to include at least about 5 wet wipes and desirably from about 16 to about 200 individual wipes, and more desirably from about 32 to about 50 wipes. The size and shape of the stack of wipes is dependent upon the size and shape of the package/dispenser and vice versa. For example, the height of an assembled stack of wipes can be about 50 mm, with a width of about 60 mm.

The plurality of wipes can be arranged in a package or dispenser in any manner which provides convenient and reliable one at a time dispensing. Suitable packages for storing and dispensing wipes may include a non-rigid container having sides with a top end portion and a bottom end portion where the sides and top and bottom end portions define a cavity within the container. The cavity includes a storage portion for wipes. The top end portion can include a resealable mechanism. A non-rigid baffle structure has a width and is located in between the resealable mechanism and the storage portion with the baffle structure positioned between opposing sides of the container spaced apart from each other. The baffle structure thereby defines a dispensing portion of the cavity overlying the storage portion of the cavity. The resealable mechanism can be any type of mechanism that allows the package to be opened, closed and reopened multiple times during the life of the package, e.g., a zipper with or without a stopper, resealable adhesive, a clip or other structure that achieves the result desired.

Although various embodiments of the invention have been described using specific terms, devices, and methods, such description is for illustrative purposes only. The words used are words of description rather than of limitation. It is to be understood that changes and variations may be made by those of ordinary skill in the art without departing from the spirit or scope of the present invention, which is set forth in the following claims. In addition, it should be understood that aspects of the various embodiments may be interchanged both in whole or in part. Therefore, the spirit and scope of the appended claims should not be limited to the description of the preferred versions contained therein.

We claim:

1. A wiping product comprising a rectangular central portion and a first and a second pair of opposed lobes continuous therewith, each lobe bisected by a longitudinal axis and having a bell-shaped curvilinear peripheral edge that terminates in a rounded tip having an edge defined by the arc of a circle, and a base that forms one side of the rectangular central portion, the circle of the first pair of opposed lobes having a radius $R1$, the circle of the second pair of opposed lobes having a radius $R2$, wherein $R1$ and $R2$ are not equal.

2. The wiping product of claim 1 wherein $R1$ is from about 10 to about 20 mm and $R2$ is from about 15 to about 30 mm.

3. The wiping product of claim 1 wherein the base of the first pair of lobes has a width $W1$ from about 20 to 40 mm and the base of the second pair of lobes has a width $W2$ from about 30 to 50 mm.

4. The wiping product of claim 1 wherein the first pair of lobes have a height $h1$ from about 10 to about 20 mm and the second pair of lobes have a height $h2$ from about 15 to about 25 mm.

5. The wiping product of claim 1 wherein the first and the second pair of opposed lobes are substantially semi-circular in shape.

6. The wiping product of claim 1 wherein the base of the first pair of lobes has a width $W1$ of about 35 mm and $R1$ is about 10 mm and the base of the second pair of lobes has a width $W2$ of about 35mm and $R2$ is about 13 mm.

7. The wiping product of claim 1 wherein the total surface area of the wipe is from about 10 to about 20 $cm2$ and the rectangular central portion comprises from about 20 to about 50 percent of the total surface area.

8. A stack of wiping products comprising a first and a second wiping product of claim 1, the first wiping product being stacked on top of the second wiping product such that the longitudinal axis of the first wiping product is orientated about 90 degrees relative to the longitudinal axis of the second wiping product.

9. A wiping product comprising a rectangular central portion and a first and a second pair of opposed lobes continuous therewith, each lobe bisected by a longitudinal axis and having a bell-shaped curvilinear peripheral edge that terminates in a rounded tip having an edge defined by the arc of a circle having a radius $R1$ or $R2$ and a base that forms one side of the rectangular central portion, wherein the first pair of lobes have a height $h1$ and the second pair of lobes have a height $h2$ and wherein $h1$ and $h2$ are not equal.

10. The wiping product of claim 9 wherein first pair of lobes terminate in a rounded tip having an edge defined by the arc of a circle having a radius $R1$ and the second pair of lobes terminate in a rounded tip having an edge defined by the arc of a circle having a radius $R2$.

11. The wiping product of claim 10 wherein $R1$ and $R2$ are equal.

12. The wiping product of claim 9 wherein the first pair of lobes have a height $h1$ from about 10 to about 20 mm and the second pair of lobes have a height $h2$ from about 15 to about 25 mm.

13. A stack of wiping products comprising a first and a second wiping product of claim 9, the first wiping product being stacked on top of the second wiping product such that the longitudinal axis of the first wiping product is orientated about 90degrees relative to the longitudinal axis of the second wiping product.

* * * * *